United States Patent
Çelik

(10) Patent No.: US 10,918,889 B2
(45) Date of Patent: Feb. 16, 2021

(54) LINAC QUALITY CONTROL DEVICE

(71) Applicant: Deniz Çelik, Istanbul (TR)

(72) Inventor: Deniz Çelik, Istanbul (TR)

( * ) Notice: Subject to any disclaimer, the term of this patent is extended or adjusted under 35 U.S.C. 154(b) by 84 days.

(21) Appl. No.: 16/320,491

(22) PCT Filed: Jul. 21, 2017

(86) PCT No.: PCT/TR2017/050330
§ 371 (c)(1),
(2) Date: Jan. 25, 2019

(87) PCT Pub. No.: WO2018/063121
PCT Pub. Date: Apr. 5, 2018

(65) Prior Publication Data
US 2020/0353290 A1    Nov. 12, 2020

(30) Foreign Application Priority Data

Aug. 9, 2016  (TR) .............................. a 2016 11175

(51) Int. Cl.
*A61N 5/10*    (2006.01)

(52) U.S. Cl.
CPC ......... *A61N 5/1075* (2013.01); *A61N 5/1049* (2013.01); *A61N 2005/1076* (2013.01); *A61N 2005/1085* (2013.01)

(58) Field of Classification Search
CPC ................ A61N 5/1075; A61N 5/1049; A61N 2005/1085; A61N 2005/1076
See application file for complete search history.

(56) References Cited

U.S. PATENT DOCUMENTS

| | | |
|---|---|---|
| 6,614,036 B1 | 9/2003 | Reinstein |
| 6,626,569 B2 | 9/2003 | Reinstein et al. |
| 7,413,345 B1 | 8/2008 | Spanswick et al. |
| 7,476,867 B2 | 1/2009 | Fritsch et al. |
| 8,845,191 B2 | 9/2014 | Ngar et al. |
| 9,283,405 B2 | 3/2016 | Wong |
| 2002/0085668 A1 | 7/2002 | Blumhofer et al. |
| 2005/0211889 A1 | 9/2005 | Varchena et al. |
| 2007/0014928 A1 | 1/2007 | Delaperriere et al. |
| 2007/0284543 A1 | 12/2007 | Rockseisen |
| 2008/0011946 A1 | 1/2008 | Suh et al. |
| 2008/0240364 A1 | 10/2008 | Main et al. |

FOREIGN PATENT DOCUMENTS

| | | |
|---|---|---|
| EP | 2701802 A1 | 3/2014 |
| WO | 2011011471 A1 | 1/2011 |

OTHER PUBLICATIONS

Wook Jae Yoo et al. "Integral T-Shaped Phantom-Dosimeter System to Measure Transverse and Longitudinal Dose Distributions Simultaneously for Stereotactic Radiosurgery Dosimetry", Sensors 2012, 12, 6404-6414; doi:10.3390/s120506404.

*Primary Examiner* — David P Porta
*Assistant Examiner* — Meenakshi S Sahu
(74) *Attorney, Agent, or Firm* — Bayramoglu Law Offices LLC

(57) ABSTRACT

A quality control device which enables all the routine quality controls of linear particle accelerators (LINACs), which are used in radiation oncology, to be performed automatically.

6 Claims, 5 Drawing Sheets

LINAC QUALITY CONTROL DEVICE

CROSS REFERENCE TO RELATED APPLICATIONS

This application is the national phase entry of International Application No. PCT/TR2017/050330, filed on Jul. 21, 2017, which is based upon and claims priority to Turkish Patent Application No. 2016/11175, filed on Aug. 9, 2016, the entire contents of which are incorporated herein by reference.

TECHNICAL FIELD

The present invention relates to a quality control device which enables all the routine quality controls of linear particle accelerators (LINACs), which are used in radiation oncology, to be performed automatically.

BACKGROUND

Today, quality control tests must be performed at certain points of installation and operation in order for the LINAC devices, which are one of the milestones in radiation oncology, to operate efficiently and accurately.
These tests may be listed as follows:
  Controlling the collimator angle indicator,
  Controlling the cross-wire stability upon collimator axis rotation,
  Conformity of cross-wire axis and radiation field axis,
  Controlling the gantry angle indicator,
  Isocenter control,
  Laser control,
  Controlling the optical distance indicator,
  Dependence of the optical distance indicator on the gantry angle,
  Controlling the indicator of field sizes,
  Controlling the conformity of the light-irradiation field,
  Arc therapy angle control,
  In addition to these tests, the measurements between the treatment table on which the LINAC device is used and the device itself must be conducted.
These tests, on the other hand, may be listed as follows:
  Controlling the angle indicator with the isocentric rotation of the treatment table,
  Conformity of the isocenter with the rotational movement of the treatment table,
  Controlling the change in the conformity of the isocenter with the rotational movement of the treatment table depending on the weight,
  Controlling the parallelism of the collimator axis with the vertical movement of the table,
  Controlling the change in the parallelism of the collimator axis with the vertical movement of the table depending on the weight,
  Asymmetrical collimator control,
  Mechanical position test of kilovolt source,
  Mechanical position test of kilovolt detector.

The mechanical quality control tests conducted using the quality control equipment in the state of the art are visual measurements performed by the user and the results of such measurement may vary from one user to another due to the human factor. Some tests include measurements that are marked on graph paper by pens and the deviation is detected visually by the user in such measurement. This, however, affects not only the accuracy but also the repeatability of the test.

For other tests, different measurement equipment is employed, and so it takes a longer time to complete all the tests.

The equipment used in the state of the art for carrying out such tests are: graph papers, needles, meters, calibrated rods of varying lengths, and digital levels.

The way of conducting the tests mentioned above using the equipment within the state of the art and the resulting technical problems are described hereinafter.

The collimator angle indicator is controlled using a digital level while the gantry is 90°. In this case, additional uncertainty occurs depending on whether the digital level is located properly. Moreover, the deviations resulting from the digital level may also have an impact on the accuracy of the measurement.
  Controlling the cross-wire stability upon collimator axis rotation is a test conducted for detecting the deviation from the center of the treatment depending on the collimator rotation. A dot is made on a paper and the deviation from this dot is tried to be detected from different collimator angles. It is a test in which the user can detect such deviations only by visual inspection, as a result of which the accuracy, precision and speed of the measurements may vary from one user to another.
  Controlling the conformity of cross-wire axis and radiation field axis refers to the detection of the conformity of the radiation field axis as obtained by irradiation at different collimator angles when the gantry is 0°. However, several drawings need to be made on the image obtained by irradiation in order to define the result of this test; therefore, the result of this measurement is dependent on the drawing skill of the user.
  The gantry angle indicator is controlled using a digital level while the gantry is 0°, 90°, 180° and 270°. Here, the technical problems are the same as those experienced in the test of controlling the collimator angle indicator.
  For isocenter control, the central image reflected on a rod attached at the end of the table is used in order to detect the deviation from the center in gantry angles. Here, the main problem is that it is challenging to detect the central projection and that the precision is entirely dependent on the user.
  The method and technical problems regarding laser control are the same as in the isocenter control test.
  For controlling the optical distance indicator, measurement is made using a rod attached to the head of the LINAC device. The treatment table is lifted until it contacts with the rod and measurements are taken from this distance. The main problem here is that the rod has a telescopic mechanism in order that its end will not damage the table. Although this prevents the rod from damaging the table, it directly affects the result of the micron-level measurement.
  The method and technical problems regarding the detection of the deviation of the optical distance indicator depending on the gantry angle are again the same as in the isocenter control test.
  In this test performed for controlling the indicator of field sizes, on the other hand, different field sizes are opened and then it is controlled whether the field sizes are opened correctly or not. The field sizes opened for this test are detected visually by the user using graph paper. The measurement results are directly dependent on the human factor, and hence the user's precision.
  In the test of controlling the conformity of the light-irradiation field, the conformity of the field, which is considered to be opened correctly in physical terms, with the radiation field is detected. During this test, it is important to accurately locate the film which detects the radiation field since the lower or higher position of the film changes the size of the field being measured.

In this test conducted for the angle control of the arc therapy, the gantry is moved at certain angles and the deviation at these angles is detected. The problem in this test is the same as that experienced while controlling the collimator angle indicator. Further, it is another important technical problem that measurement cannot be made at intermediate angles. For example, only the deviation at 0° and 90° can be detected in case of 0° and 90° arc control. As a result, it is not possible to detect the deviations and sizes of deviations at the angles at interval values.

The conformity of the isocenter with the rotational movement of the treatment table is the test conducted for detecting the deviation from the isocenter depending on the rotational movement of the treatment table and the technical problem and the uncertainty in this test are the same as in the test of controlling the cross-wire stability upon collimator axis rotation.

The test for controlling the change in the conformity of the isocenter with the rotational movement of the treatment table depending on the weight, on the other hand, is a different version of the test of controlling the conformity of the isocenter with the rotational movement of the treatment table in which a weight is placed on the table during the test. The reason for placing a weight on the table is to simulate the weight of the patient to lie on the table during the therapy. Similar technical problems are experienced here.

Controlling the parallelism of the collimator axis with the vertical movement of the table is the test used for detecting the deviation from the isocenter based on the vertical movement of the table. The technical problem and the uncertainty in this test are the same as in the test of controlling the cross-wire stability upon collimator axis rotation.

The test for controlling the change in the parallelism of the collimator axis with the vertical movement of the table depending on the weight, on the other hand, is a different version of the test of controlling the parallelism of the collimator axis with the vertical movement of the table in which a weight is placed on the table during the test. The reason for placing a weight on the table is to simulate the weight of the patient to lie on the table during the therapy. Similar technical problems are experienced here.

It is determined in this test, which is performed for controlling the asymmetrical field, whether a coincidence resulting from field combination is present or not. The technical problem and the uncertainty in this test are the same as in the test of controlling the conformity of the light-irradiation field.

In the mechanical position test of the kilovolt source, ruler measurement is made for confirming the position of the source at distances of 80, 90 and 100 cm. The main problem in measurements is the precision and accuracy errors resulting from the ruler-based measurement.

In the mechanical position test of the kilovolt source detector, ruler measurement is made for confirming the position of the source at distances of −30, −50 and −75 cm. The main problem in measurements is the precision and accuracy errors resulting from the ruler-based measurement.

Apart from the manual tests in the state of the art which are described in detail above, there also exist automated systems which have been developed. The European Patent Application No. EP2701802 and the U.S. Pat. Nos. 8,845, 191, 9,283,405, 6,614,036, 6,626,569 and 7,476,867 may be given as examples to these systems.

In order to clearly describe the aforementioned procedures, the explanations as to the components used in the related technical field are made below:

Gantry: It is a treatment head which may be circularly rotated around the patient and in which electrons and x-rays are generated.

Collimator: It is a type of protection block which is disposed in the gantry and used for shaping the therapy area by filtering x-rays.

LINAC: Known as Linear Particle Accelerator (LINAC), this device generates high energy x-rays and electrons. The electrons ejected from the metal target under high voltage are accelerated within the electromagnetic field such that they will have a higher energy. While the high energy electron beam can be used in surface tumors, the high energy x-rays obtained as a result of making them hit a target are used in the treatment of deeply located tumors.

Isocenter (cross-wire): The point of treatment center in which the rotational axes of the gantry, collimator and couch of the LINAC device coincide.

Arc Therapy: A radiotherapy method in which the LINAC device operates by rotating around the patient and the shape and intensity of the radiation beams are constantly changed.

ODI (Optical Distance Indicator): It is an optical distance indicator which allows digital display of the distance with respect to the source in LINAC device.

SUMMARY

The most important and common technical problem in the tests conducted with the equipment in the state of the art which have been described above in detail is that they are vulnerable to faults resulting from human errors because they are performed manually.

In addition to this, the so-called IsoCheck, a measuring instrument, is used in some of the mechanical measurements. Prior to starting measurements using this instrument, it is required to be adjusted using the digital level such that it will be properly positioned and be parallel with respect to the gantry; otherwise, uncertainty may occur in the measurements.

Not only making these adjustments is time-consuming but also positioning of the device may differ from one user to another. The device according to the invention, however, automatically adjusts its center and parallelism with respect to the gantry, thereby not only saving on time but eliminating the uncertainty based on the installation of the device as well.

Moreover, all of these tests are performed automatically thanks to the quality control device according to the invention and measurement results are obtained with more precision and accuracy when compared to manual methods.

The tests carried out using a digital level in the state of the art are performed using 2 different laser distance measuring systems and G-sensor (gyrosensor/gyroscope) in the device according to the invention and the angular deviations in the gantry can be detected with high precision.

The tests conducted by a dot made on the paper in the state of the art are performed using optical sensors (photodiodes)

in the device according to the invention and the movements of the table, collimator and gantry are digitally monitored, thereby detecting the deviations with high precision.

Thanks to the device according to the invention, the tests performed by means of a radiographic film positioned using LINAC variants (laser, optical distance indicator, isocenter) in the state of the art are performed using a radiographic film properly positioned by means of laser distance sensors instead.

Rather than the detection made by the central image reflected on a rod which is attached to an end of the table with a view to detect the deviations from the center at different gantry angles in the state of the art, the deviations are digitally detected with high precision using optical sensors (photodiodes) with the device according to the invention.

The uncertainty regarding the test of controlling the optical distance indicator, the mechanical position test of the kilovolt source and mechanical position test of the kilovolt detector can be eliminated using a laser distance meter in the device according to the invention.

BRIEF DESCRIPTION OF THE DRAWINGS

The drawings illustrating the LINAC quality control device developed with the present invention are given below for a better understanding of the invention.

DESCRIPTION OF THE PART REFERENCES

Figure 1A:
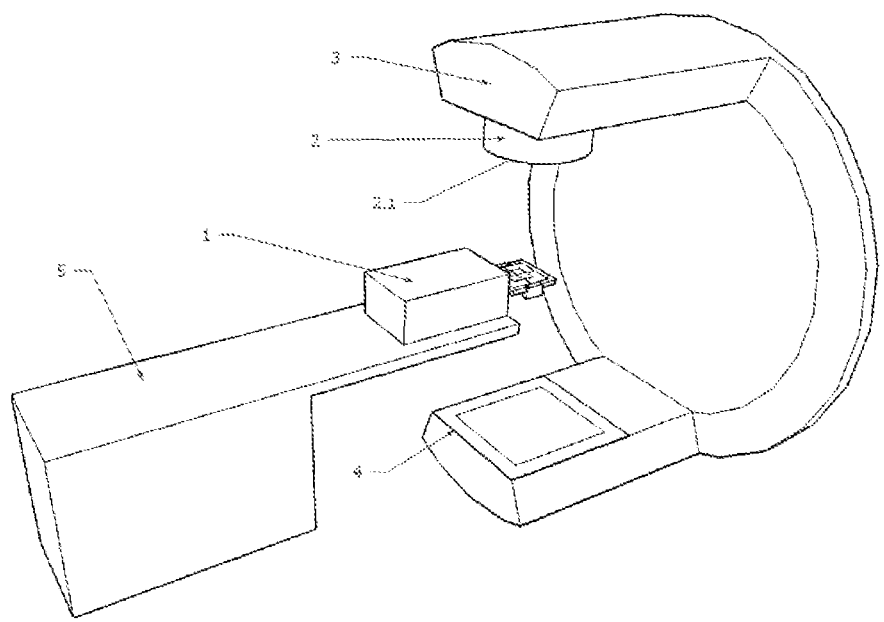
FIG. 1A—Perspective view of the LINAC device and the treatment table of the LINAC device.
Figure 1B:
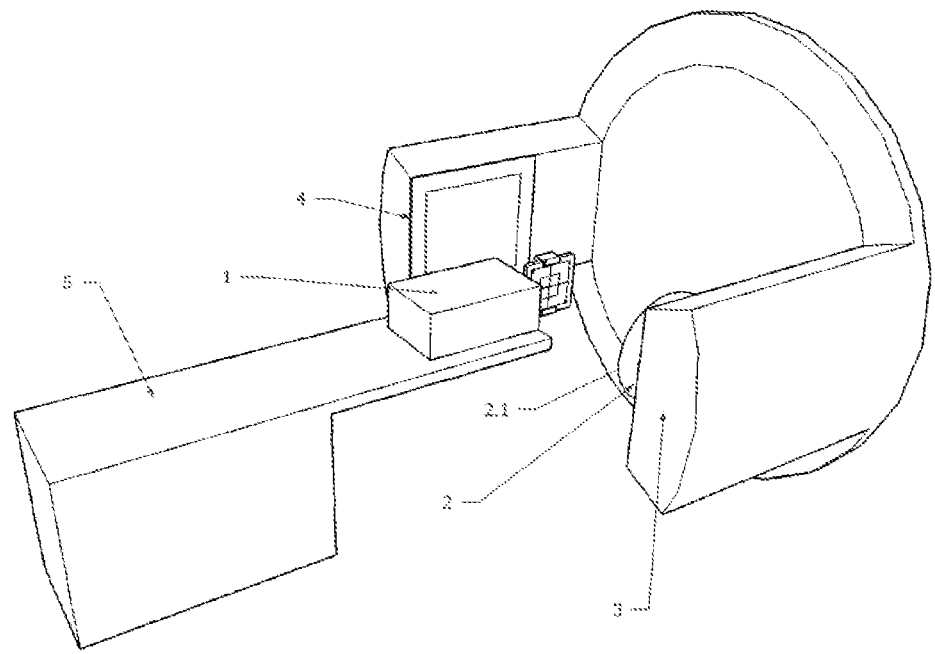
FIG. 1B—Perspective view of the treatment head at 90°.
Figure 1C:
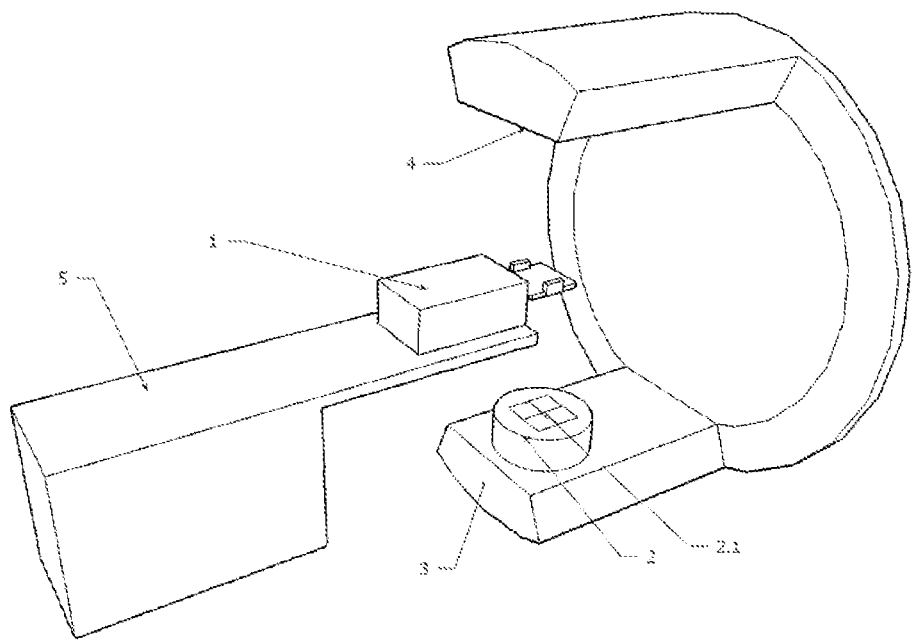
FIG. 1C—Perspective view of the treatment head at 180°.
Figure 1D:
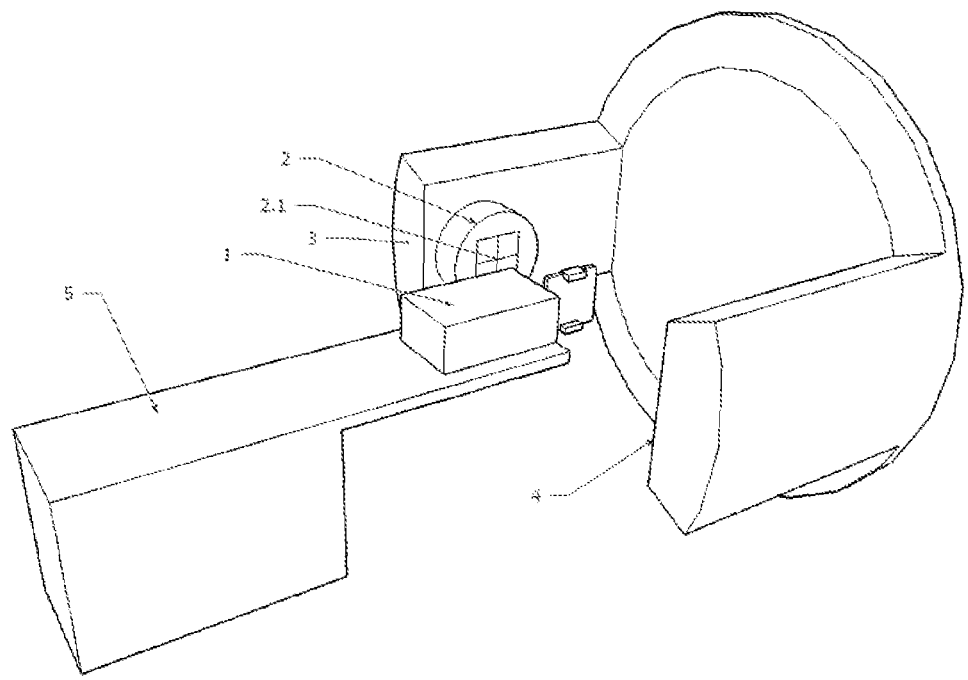
FIG. 1D—Perspective view of the treatment head at 270°.
Figure 1E:
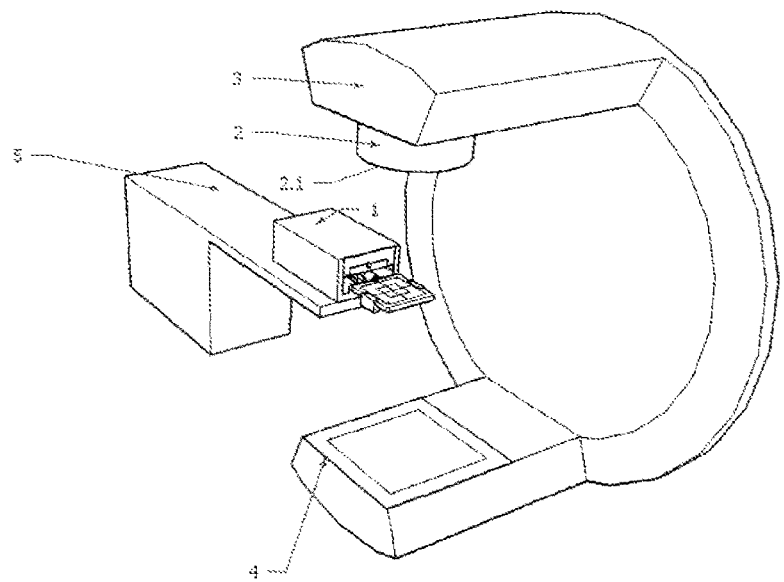
FIG. 1E—Perspective view of the treatment table at 90°.
Figure 1F:
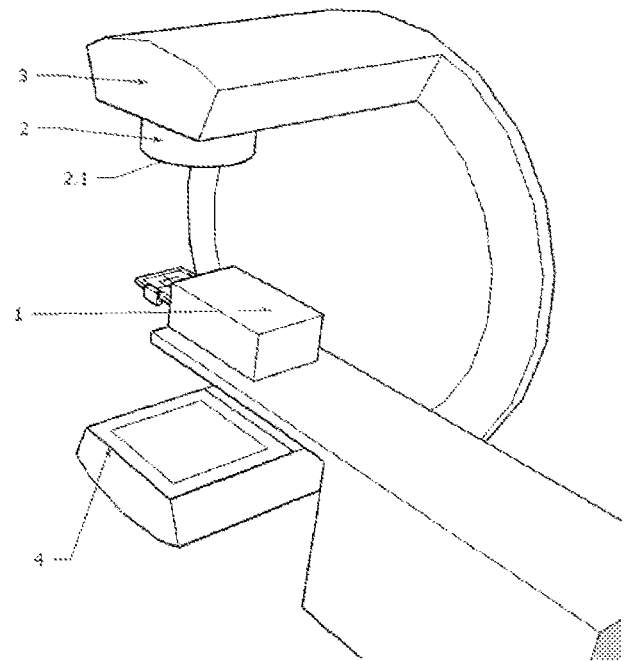
FIG. 1F—Perspective view of the treatment table at −90°.
Figure 2:
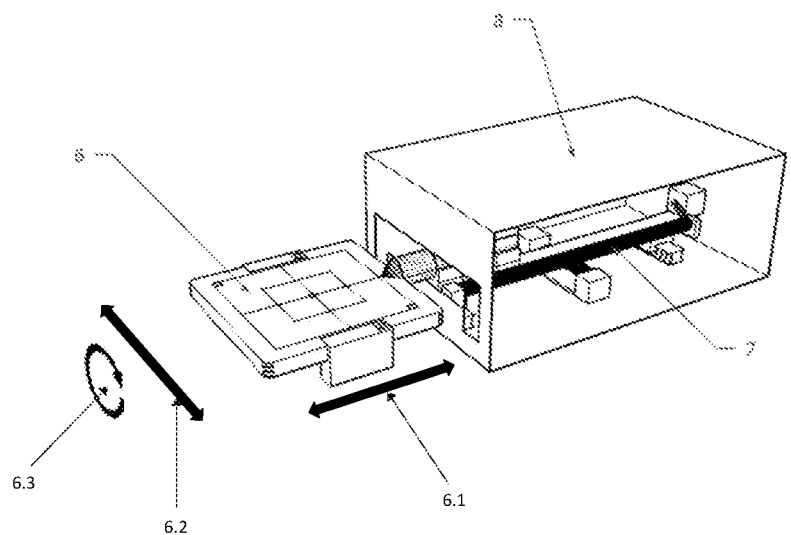
FIG. 2—Perspective view of the LINAC quality control device according to the invention.

The parts/portions/components which are shown in the drawings illustrating the LINAC quality control device developed with the present invention for a better understanding of the invention are enumerated individually and the reference numbers corresponding thereto are given below.

1. LINAC quality control device
2. Collimator
    2.1 Cross-wire (isocenter) Central axis of the area in which treatment will be made
3. LINAC treatment head rotatable 360° around the patient
4. Portal imaging system which allows taking images of the patient before and during the treatment
5. Treatment table capable of moving at 6 axes (back-and-forth, up-and-down, horizontal, rotational, angular, pitch) on which the patient lies during the treatment
6. Sensor panel
    6.1. Back-and-forth movement of the panel
    6.2. Horizontal movement of the panel
    6.3. Rotational movement of the panel
7. Motorized system capable of moving the sensor panel at 3 axes
8. Impact-resistant casing of the LINAC quality control device
9.22. Optical sensor 1
9.23. Optical sensor 2
9.24. Optical sensor 3
9.25. Optical sensor 4
9.26. Optical sensor 5
9.27. Optical sensor 6
9.28. Optical sensor 7
9.29. Optical sensor 8
9.30. Optical sensor 9
9.31. Optical sensor 10
9.32. Central optical sensor 11
9.33. Optical sensor 12
9.34. Optical sensor 13
9.35. Optical sensor 14
9.36. Optical sensor 15
9.37. Optical sensor 16
9.38. Optical sensor 17
9.39. Optical sensor 18
9.40. Optical sensor 19
9.41. Optical sensor 20
9.42. Optical sensor 21
10.3. Laser distance sensor 1
10.4. Laser distance sensor 2
11.3. G-sensor 1
11.4. G-sensor 2
12.1. Rotational movement motor
12.2. Horizontal movement motor
12.3. Back-and-forth movement motor
13.1. Back-and-forth movement gear
13.2. Horizontal movement gear
14.1. Back-and-forth movement motor bearing system
14.2. Horizontal movement motor bearing system
15.1. Linear bearing system accommodating the horizontal movement motor
15.2. Linear bearing system accommodating the back-and-forth movement motor
16. Belt and pulley mechanism of rotational movement
17. Optical sensor
18. 2 mm hole made on the optical sensor

DETAILED DESCRIPTION OF THE EMBODIMENTS

The primary embodiment of the quality control device (1) according to the invention which has been developed in order for all the routine quality controls of linear particle accelerators (LINACs), which are used in radiation oncology, to be performed automatically comprises the following components.

Sensor Panel (6):

The sensor panel (6) which may be positioned in the casing (8) of the quality control device (1) when not in use and which, during the controlling process, can be made to assume its operational position by protruding from the end portion of the casing (8), is provided thereon with the following such that the required measurements will be performed:

At least 21 optical sensors (9.1-9.21),
At least 2 laser distance sensors (10.1 and 10.2),
At least 2 G-sensors (11.1 and 11.2),
At least one optical sensor (17) which is located at a depth of 1 mm from the surface of the panel (6), and A 2 mm hole (18) made in the portion of the panel (6) surface coming over the optical sensor (17) in order to provide the viewpoint of the sensor (17).

All of said sensors are disposed on one surface of the panel (6) and the panel (6) surface on which such sensors are located is entirely flat.

Figure 3:
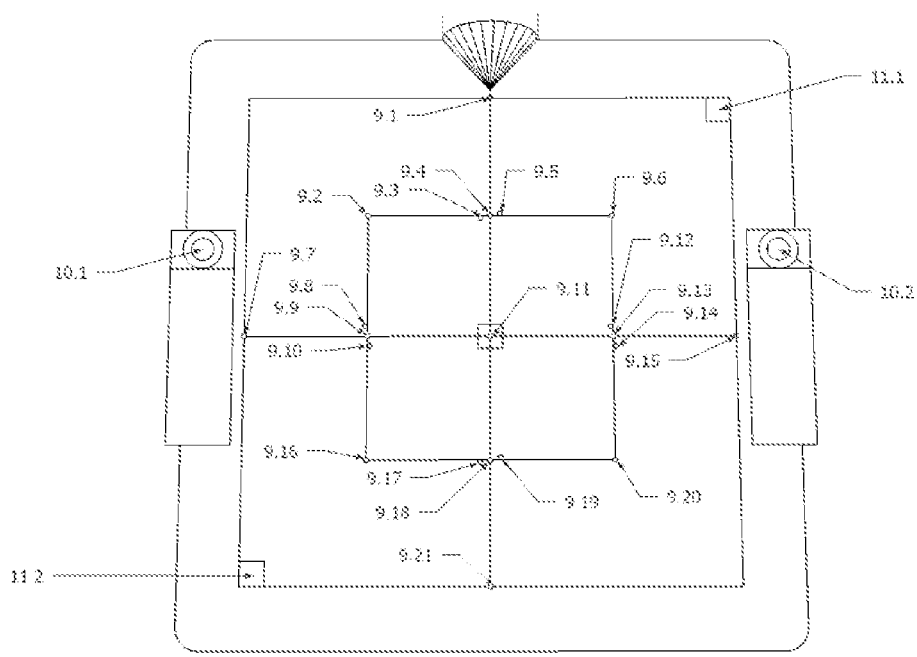
FIG. 3—Top view of the sensor panel in the LINAC quality control device according to the invention.
Figure 4:
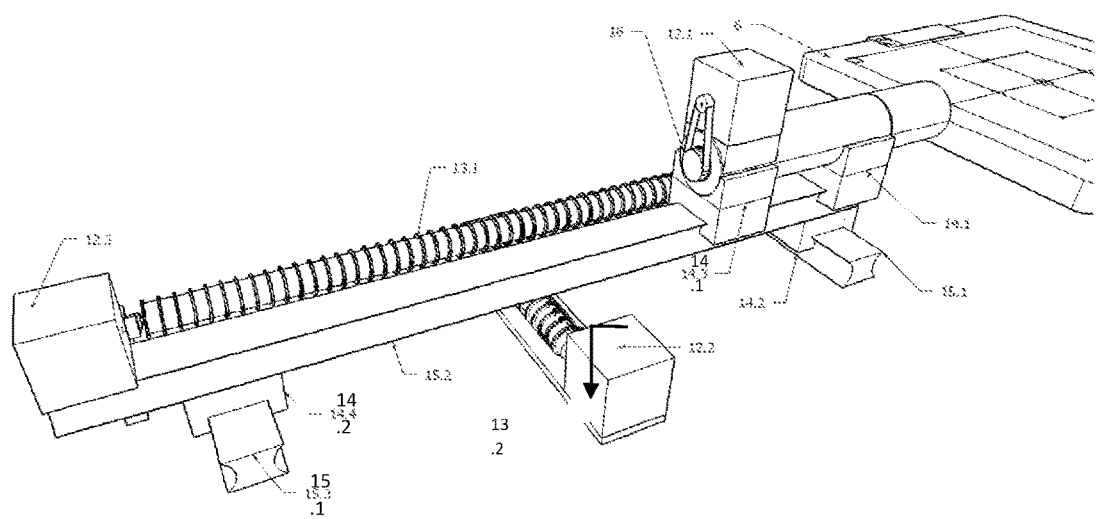
FIG. 4—Perspective view of the motorized systems moving the sensor panel in the LINAC quality control device according to the invention.
Figure 5:
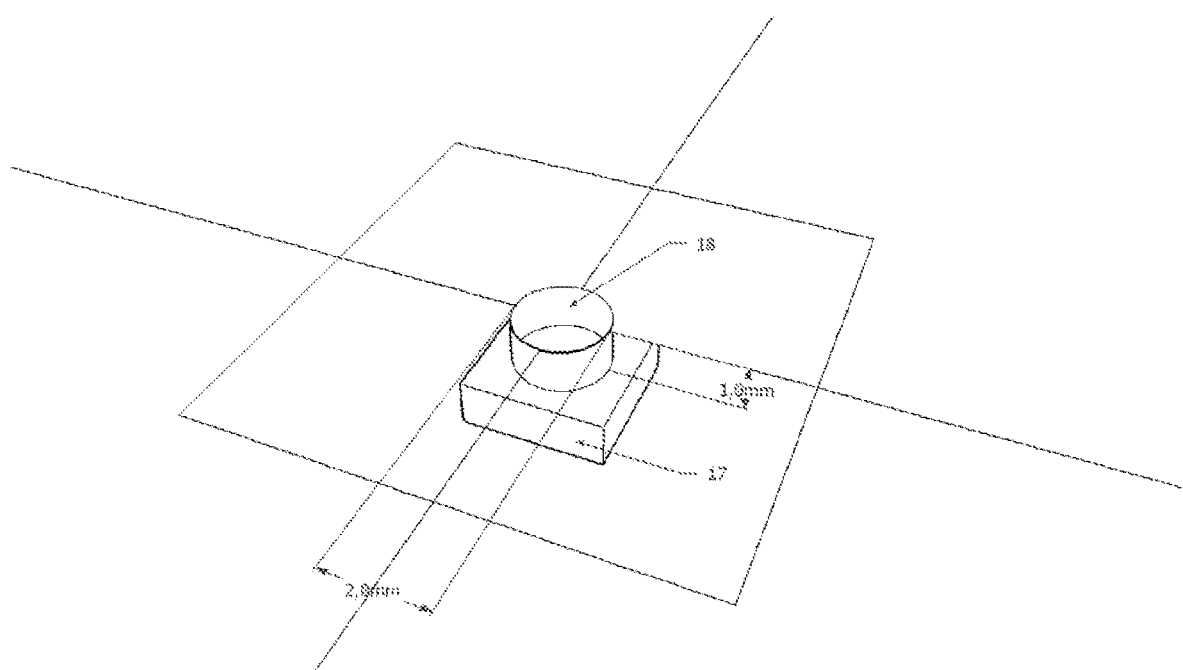
FIG. 5—Perspective view of the optical sensor system which is located at a certain depth from the surface of the sensor panel in the LINAC quality control device according to the invention.

The positioning of the sensors is as shown in FIGS. 3 and 5 in the primary embodiment of the invention; however, they may be positioned differently in different embodiments of the invention.

Thanks to the motorized system (7) to which the sensor panel (6) is connected, the latter is capable of moving at 3 axes: back-and-forth (6.1), horizontal (6.2) and rotational (6.3).

Motorized System (7):

The motorized system (7), which is the mechanism that enables the sensor panel (6) to move at 3 axes, i.e. back-and-forth, horizontal and rotational axes, further allows the panel (6) to be introduced into and protrude from the casing (8) (6.1), and when in protruded position, to move in horizontal direction (6.2) and rotationally (6.3).

The motorized system (7) within the casing (8) comprises:
At least 1 rotational movement motor (12.1) allowing the rotational movement of the panel (6),
At least 1 horizontal movement motor (12.2) allowing the movement of the panel (6) in horizontal plane,
At least 1 back-and-forth movement motor (12.3) allowing the back-and-forth movement of the panel (6),
At least 1 back-and-forth movement gear (13.1) transferring the drive of the back-and-forth movement motor (12.3) to the panel (6),
At least 1 horizontal movement gear (13.2) transferring the drive of the horizontal movement motor (12.2) to the panel (6),
Back-and-forth movement motor bearing system (14.1) accommodating the back-and-forth movement motor (12.3),
Horizontal movement motor bearing system (14.2) accommodating the horizontal movement motor (12.2),
Horizontal movement motor linear bearing system (15.1) accommodating the horizontal movement motor (12.2),
Back-and-forth movement motor linear bearing system (15.2) accommodating the back-and-forth movement motor (12.3), and
At least one belt and pulley mechanism (16) of rotational movement which transfers the drive of the rotational movement motor (12.1) to the panel (6).

Casing (8):

It serves as a shell which provides protection against impacts, in which the motorized system (7) is disposed and the sensor panel (6), when not in use, is positioned.

In the primary embodiment of the invention, the casing (8) is made of any type of metal alloy, e.g. aluminium or steel; furthermore, it may as well be made of polymer material according to the application area.

What is claimed is:

1. A quality control device for performing automatic routine quality controls of linear particle accelerators (LINACs) used in radiation oncology, comprising:
a sensor panel positioned in a casing of the quality control device when not in use, wherein, the sensor panel is configured to protrude from an end portion of the casing into an operational position during controlling process;
wherein, the sensor panel comprises
at least twenty one first optical sensors,
at least two laser distance sensors,
at least two G-sensors,
at least one second optical sensor located at a depth of 1 mm from a surface of the sensor panel, and
a 2 mm hole made in a portion of the sensor panel surface coming over the at least one second optical sensor in order to provide a viewpoint of the at least one second optical sensor;
motorized system is disposed in the casing and is configured to move the sensor panel at three axes: back-and-forth, horizontal and rotational; the motorized system comprises
at least one rotational movement motor configured for rotational movement of the sensor panel,
at least one horizontal movement motor configured for the movement of the sensor panel in a horizontal plane,
at least one back-and-forth movement motor configured for the back-and-forth movement of the sensor panel,
at least on back-and-forth movement gear transferring the drive of the back-and-forth movement motor to the sensor panel,
at least one horizontal movement gear transferring the drive of the horizontal movement motor to the sensor panel,
a back-and-forth movement motor bearing system accommodating the back-and-forth movement motor,
a horizontal movement motor bearing system accommodating the horizontal movement motor,
a horizontal movement motor linear bearing system accommodating the horizontal movement motor,
a back-and-forth movement motor linear bearing system accommodating the back-and-forth movement motor, and
at least one belt and pulley mechanism of rotational movement which transfers the drive of the rotational movement motor to the sensor panel; and
wherein, the casing serves as a shell providing protection against impacts.

2. The quality control device according to claim 1, wherein all of the sensors are disposed on a first surface of the sensor panel.

3. The quality control device according to claim 2, wherein, the first surface of the sensor panel is entirely flat.

4. The quality control device according to claim 1, wherein, the casing is made of metal alloy.

5. The quality control device according to claim 1, wherein, the casing is made of a polymer material.

6. The quality control device according to claim 4, wherein, the metal alloy is aluminium or steel.

* * * * *